United States Patent [19]
Steffee

[11] 4,011,603
[45] Mar. 15, 1977

[54] FINGER JOINT IMPLANT
[75] Inventor: Arthur D. Steffee, Gates Mills, Ohio
[73] Assignee: Laure Prosthetics, Inc., Portage, Mich.
[22] Filed: Aug. 29, 1975
[21] Appl. No.: 608,849
[52] U.S. Cl. ................................. 3/1.91; 3/1.911; 128/92 C
[51] Int. Cl.² .......................................... A61F 1/24
[58] Field of Search ...................... 3/1, 1.9–1.913; 128/92 C, 92 CA

[56] References Cited
UNITED STATES PATENTS

| 3,506,982 | 4/1970 | Steffee | 3/1.91 |
| 3,795,922 | 3/1974 | Herbert et al. | 3/1.911 |

FOREIGN PATENTS OR APPLICATIONS

| 1,047,640 | 7/1953 | France | 128/92 C |
| 2,064,432 | 7/1972 | Germany | 3/1.911 |
| 1,902,700 | 8/1970 | Germany | 3/1.91 |

*Primary Examiner*—Ronald L. Frinks
*Attorney, Agent, or Firm*—Woodhams, Blanchard & Flunn

[57] ABSTRACT

Endoprosthetic joint particularly one permitting no appreciable adduction or abduction. There is provided an endoprosthesis for ginglymus joints comprising a first part made from a metal inert to the human body and having a substantially cylindrical head. A second part is provided of molded plastics material having a socket of substantially cylindrical shape for receiving said head. A ridge is provided around the entire perimeter of the aperture through which access to said socket is obtained, which ridge is of dimension to permit the parts to be snapped together manually but to provide substantial resistance against their becoming unsnapped. Further, the cylindrical head is only a clearance distance shorter than the corresponding dimension of the socket whereby swing motion of said head within said socket is substantially prevented.

7 Claims, 10 Drawing Figures

U.S. Patent  Mar. 15, 1977  4,011,603

FINGER JOINT IMPLANT

FIELD OF THE INVENTION

This invention relates to endoprosthetic joints and more particularly to an endoprosthesis for ginglymus joints which will be durable and capable of withstanding strenuous usage; which may be solidly implanted into the body of a subject human or animal and resist displacement, twisting or migration with respect to the surrounding bone; which will closely approximate the motion of a healthy natural joint; and which will be relatively easy to insert and thereafter cause a minimum of pain, discomfort or restriction of activity in the subject.

BACKGROUND OF THE INVENTION

The subject of endoprosthetic joints has received a great deal of attention over the past several years and has particularly received much attention in recent years due in part to the availability of improved materials inert to human or animal bodies and to improved techniques for manipulating same. However, in spite of such intensive study, the endoprosthetic joints previously available, while in many cases satisfactory to a limited degree, are far from fully satisfactory and intensive work is continuing for the further improvement of such prostheses.

In one particular area, namely that of the ginglymus joints found in phalangeal joints and in the metacarpol phalangeal joint, previous efforts, while considerable and to a degree satisfactory, have still left considerable to be desired. Among the problems to be faced in connection with such joints, it is necessary to provide a joint which permits motion in only one plane and which to this end will have a considerable amount of resistance against motion out of such plane. For example, in many finger manipulations, considerable side pressure is placed upon the ends of the fingers, and especially on the thumb by the forefinger in some grasping manipulations, and the endoprosthetic joint must be able to resist such force. On the other hand, in such cases where during the implanting procedure it is preferable to implant each part of the joint separately, it is necessary that the two parts can be snapped together with a minimum of effort after the implanting has been completed.

In my earlier U.S. Pat. No. 3,506,982, I dealt with this same problem and provided a joint designed for movement in only a single plane together with means by which same could be firmly and reliably implanted into appropriate bones on either side of a ginglymus, as a phalangeal, joint. Endoprosthetic joints made according to this patent have proven extremely successful and have been implanted successfully in large numbers. However, in a continuing effort to improve products of this nature and recognizing that the joint of U.S. Pat. No. 3,506,982 normally provides for at least a limited degree of adduction and abduction, I have now developed a joint wherein the motion is firmly confined to a single plane and no abduction or adduction whatever is permitted. In this connection, I have proceeded from the broad suggestion contained in said patent relative to utilizing a more cylindrical protuberant head than set forth in such patent and have now developed same fully to an operative form and disclose same herewith.

Accordingly, the objectives of the invention include:

1. To provide a prosthesis for ginglymus joints which can be assembled or disassembled as needed during the implanting procedures but when assembled will provide strong resistance against a laterally applied force.
2. To provide a prosthesis, as aforesaid, which will be of sufficiently simple design as to be readily made by normal manufacturing procedures.
3. To provide a prosthesis, as aforesaid, which can be readily and easily implanted into bone structure on either side of a joint, such as a phalangeal joint.
4. To provide a prosthesis, as aforesaid, which will be strong and sturdy in operation and enable the user to perform all normal finger functions.
5. To provide a prosthesis, as aforesaid, which closely approximates the normal phalangeal joints.

Other objects and purposes of the invention will be apparent to persons acquainted with devices of this general type upon reading the following specification and inspection of the accompanying drawings.

SUMMARY OF THE INVENTION

Figure 1:
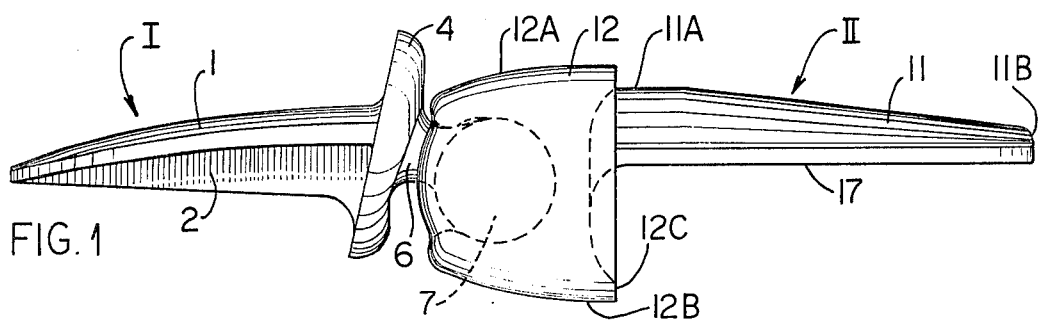
FIG. 1 shows a side view of an endoprosthetic joint embodying the invention.

In meeting the objects and purposes above outlined, an endoprosthesis has been provided comprising first and second components, one made of a biologically inert metal and the other made of a plastics material, of which each is provided with a prong for insertion into the bone structure on each side of the joint being replaced. A first said component is provided with a head of substantially cylindrical shape and the second component is provided with a socket accessible through an aperture, which aperture has a ridge around at least a portion of, and preferably all of, its perimeter for effecting a snap action in the assembly or separation of said components. The length of said cylindrical head is only a clearance distance less than the corresponding length of said socket so that abduction and adduction of the resulting joint is strongly resisted and substantially prevented. The corners of said aperture are radiused on radii larger than the corresponding corners of the head so as to provide webs acting on the corners of said head for further assisting in holding same in place after assembly of the components.

DETAILED DESCRIPTION

Referring now to the drawings in more detail, there is shown in the drawings an endoprosthetic joint for the replacement of a phalangeal joint in a human hand which is but one example of a prosthetic device constructed in accordance with the teachings of the present invention. Same may be modified as needed to comprise prostheses for other ginglymus joints including a knee joint.

The illustrative joint shown in FIGS. 1 and 2 comprise the headed member I cooperating with a socketed member II both of which will be described in detail hereinafter.

Referring first to the headed member there is shown a stem portion 1 having a rigidifying or reinforcing fin 2, said stem portion terminating at one end in a rounded end 3 and at the other end in a generally disk-shaped anchor portion 4. The stem portion 1 preferably extends at a slight angle to the plane of the disk-shaped anchor portion 4 and the reinforcing fin 2 tapers from a relatively wide section adjacent the anchor portion 4 to a blending with the lower surface of the stem portion 1 adjacent the end 3. The precise details of the relative sizes of the stem portion 1, the anchor portion 4, the angular relationship therebetween and the size and tapering of the fin portion 2 while important are all well within the known art and need no further detailing here.

A neck portion 6 protrudes from the anchor portion 4 at approximately the midpoint thereof and terminates in a generally cylindrical head 7. The head 7 is of substantial width, here nearly the width of the anchor portion 4 and of a diameter approximately one-half to two-thirds that of the anchor portion 4. The neck portion 6 is of width nearly equal to the length of the cylindrical head 7 and more specifically is as wide as possible while permitting engagement of the ends 7A and 7B of the cylindrical head by the edges of socket means as further set forth hereinafter.

Figure 4:
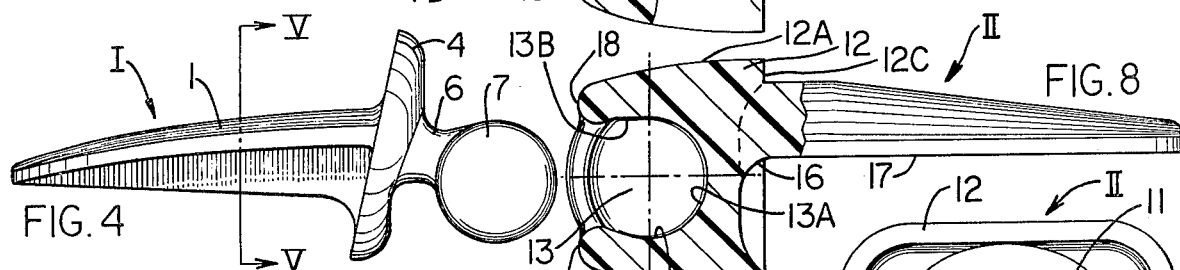
FIG. 4 is a side view of the part shown in FIG. 3.
Figure 7:
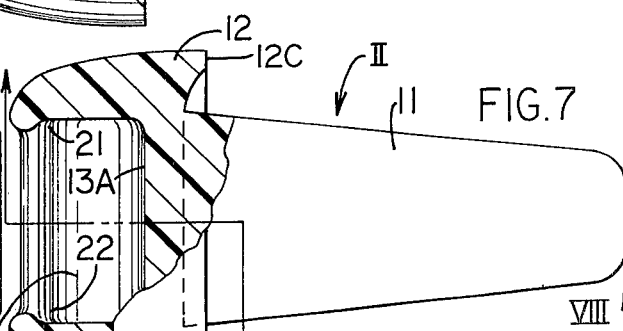
FIG. 7 is a top, partially sectioned, view of the other part of the joint shown in FIG. 1.
Figure 8:
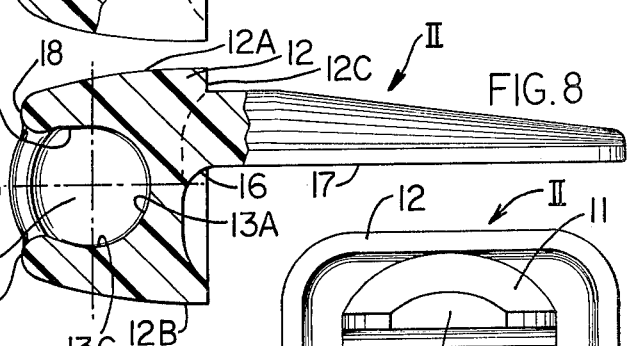
FIG. 8 is a side partially sectioned view of the part shown in FIG. 7, the section portion being taken on the line VIII—VIII of FIG. 7.
Figure 5:
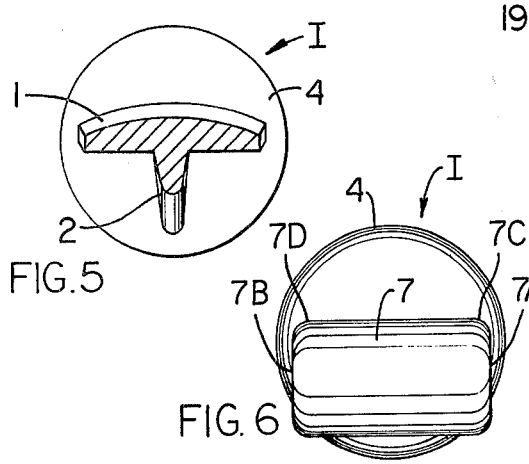
FIG. 5 is a section taken on the line V—V of FIG. 4.
Figure 6:
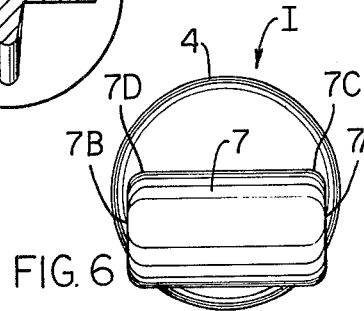
FIG. 6 is an elevational view from the rightward end of FIG. 4.
Figure 9:
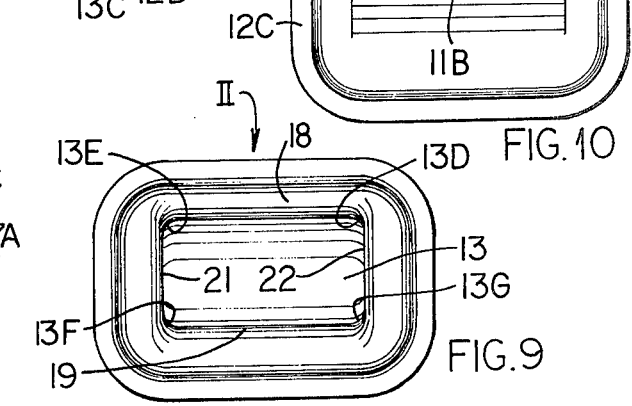
FIG. 9 is a view from the leftward end of the part shown in FIG. 7.
Figure 10:
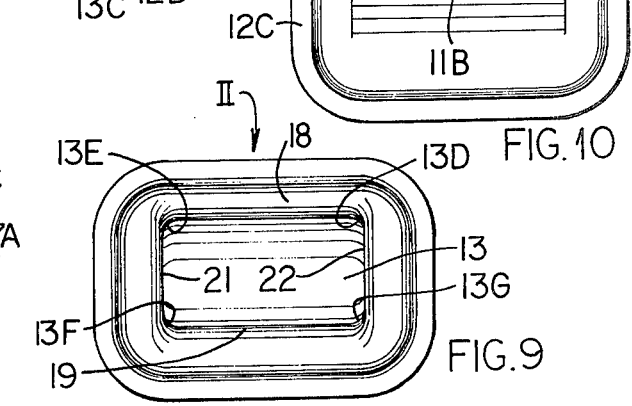
FIG. 10 is a view from the rightward end of the part shown in FIG. 7.

The positioning of the neck 6 with respect to the cylindrical head 7 is in an upper quadrant thereof as best shown in FIG. 4 in order that, as further developed hereinafter, the head portion I can rotate downwardly from the position shown in FIG. 1 to an angular relationship with the socket portion II. By appropriate design of the head 7, neck 6 and lip 19, the said angular relationship can be determined as desired, usually in the range of from 30° to 90° and in this embodiment about 50°. Upward rotation of the head portion I is limited by interference between the anchor portion 4 and the lip 18.

Turning now to the socket portion II as illustrated in FIGS. 7–10, there is here provided a stem portion 11 which is relatively wide and thin and tapers from a relatively thicker portion at the end 11A thereof to a relatively thinner section at the end 11B thereof. Said socket member II has a body 12 fixed to the end 11A of the stem 11 and for reasons more fully developed hereinafter, said stem is affixed to the body 12 near the upper side of such body. In this particular embodiment the center of the stem 11 is approximately one-fourth of the distance from the top surface 12A to the bottom surface 12B of the body 12 and its rear face 12C is substantially perpendicular to the plane of the bottom face 17 of the stem 11.

Positioned within the body 12 is a socket 13 which is in this embodiment centered in a plane approximately midway between the above-mentioned surfaces 12A and 12B. The inner portion of the socket 13 defines substantially a semicylindrical surface 13A terminating at least approximately at a diameter therethrough denoted for identification as the vertical diameter, same being essentially parallel with the rear face 12C of the body 12. The surface 13B of one side of said socket, in this embodiment the upper side, comprises a continuation of the semicylindrical curved surface 13A for a short distance, as 10°–15°, and then curves outwardly and upwardly to define a lip 18 which then blends into the upper surface of the body 12.

The lower side 13C of the socket 13 similarly continues from the vertical diameter, and comprises a continuation of the semicylindrical surface 13A for a short distance, namely approximately another 10°–15° beyond said vertical diameter, and then curves outwardly and downwardly to define the lip 19 and thence further downwardly to blend into the lower surface of the body 12. Thus, the minimum spacing at the entrance into the socket 13 is slightly less than the diameter thereof in order to provide at least a portion of the holding means retaining the head 7 within the socket 13. The precise dimensioning of the lips 18 and 19 will be chosen in view of the materials being used to permit manual snapping of the head 7 into the socket 13 but to maximize the resistance to escape of the head therefrom.

Figure 3:
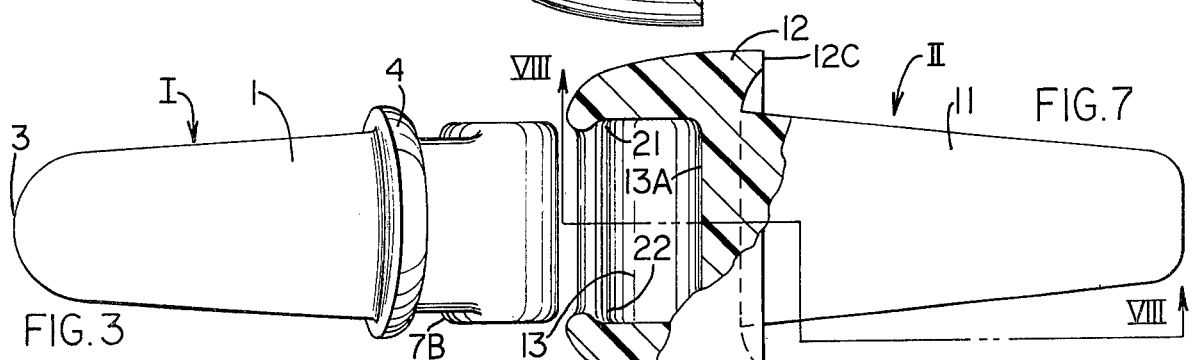
FIG. 3 is a top view of a first part of the joint shown in FIG. 1.

Turning now to FIG. 7, it will be again recognized that the socket 13 includes a semicylindrical portion 13A referred to above and further that the lateral edges thereof 21 and 22 bulge slightly toward each other to provide ridges defining a somewhat narrowed entrance for the head 7 into the socket 13. With the head 7 being only a clearance distance shorter axially than the socket 13 (in one specific embodiment the head 7 measures 0.335 inch along its central axis and the corresponding measurement for the socket 13 is 0.365 inch) it will be apparent that the leftward (as appearing in FIG. 3) portion of said head will snap past the ridges at the edges 21 and 22 and said head will be retained in the socket thereby. Again, the precise dimensioning of the ridges is chosen in a known manner according to the material being used to permit manual snapping of the head 7 into the socket 13 but to maximize the resistance to escape of the head therefrom.

Lastly, the corners 13D–G of the aperture opening into socket 13 are radiused on radii slightly larger than the radii defining the curved corners 7C and 7D of the head 7. This results in resilient corner webs which provide enlarged areas for resiliently holding the head within the socket. Thus, the ridges formed at the top, bottom and sides to retain the head 7 in the socket 13 are continued at each corner and are effective in spite of the slight rounding of the corners 7C and 7D.

Thus, regardless of slight variations in tolerances during manufacturing operations, the head will be held firmly and without play within the socket 13. Further, while the head can be inserted into and withdrawn from the socket 13 without undue effort if desired by the surgeon during an implanting procedure, there will nevertheless be considerable resistance to such withdrawal and under no conditions of ordinary use is the head 7 likely to be accidentally displaced from the socket 13. Nevertheless, the cooperation of the cylindrical parts, together with proper choice of materials such that one thereof is self-lubricating, renders the hinge motion thereof easy and smooth.

It will be further apparent that due to the snug relationship between the cylindrical head 7 and the partially cylindrical socket 13, and the fact that said head is little if any more than clearance interference distance shorter than said socket, it will be virtually impossible to move said joint in an adduction and abduction manner.

Figure 2:
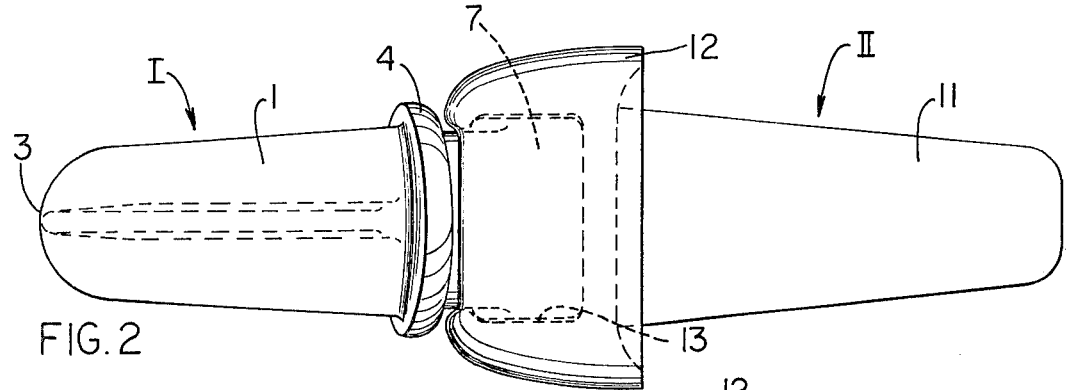
FIG. 2 is a top view of the joint of FIG. 1.

In use, the parts are snapped together as shown in FIGS. 1 and 2 and respective stems 1 and 11 inserted into the phalanges in a manner already known.

It will be noted from the several figures that the center of rotation for both the head 7 and socket 13 is positioned substantially below the center plane of the stems 1 and 11. This permits a more natural positioning of the tendons and muscles with respect to the prosthesis structure and a more naturally operating joint than is possible when said center of rotation is on or very nearly on such central plane, such as shown in FIG. 1 of my U.S. Pat. No. 3,506,982. While the amount of such offset can vary according to the details of a particular use, it will normally be at least one-quarter the diameter of the head 7 and socket 13 and may in many cases be even greater.

While a variety of materials are available which are effective for this purpose, they must in all cases be materials which are inert to the body, stiff enough to provide the necessary mechanical strength and capable of providing an easily operated hinge action. In the present embodiment, the head member I is made from a chromium cobalt alloy identified by the generic trade designation of ASTM F-75. The socket portion II is preferably made from any of several plastics materials having sufficient self-lubricating properties as to make them readily movable with respect to the head portion, such as any of several high density polyethylene materials.

Although particular preferred embodiments of the invention have been disclosed in detail for illustrative purposes, it will be understood that variations or modifications of the disclosed apparatus, including the rearrangement of parts, lie within the scope of the present invention.

The embodiments of the invention in which an exclusive property or privilege is claimed are defined as follows:

1. An implantable type endoprosthesis for a ginglymus joint, and in particular a finger joint, made of materials which are substantially inert to the body, comprising:

a protuberant headed member comprising a stem portion for affixing said member in a bone, a neck portion on one end of said stem portion, and a protuberant head portion on said neck portion, said protuberant head portion being of cylindrical shape and having an axial length which is greater than its diameter;

a socketed member comprising a stem portion for affixing said member in a bone, and a polymeric socket portion at one end of said stem portion having wall portions defining an at least partially semicylindrical socket cavity of radial and axial dimensions for snugly embracing said cylindrical head portion, said socket cavity being accessible through a generally rectangular aperture which is elongated in a direction parallel to the axial directions of said cylindrical head portion and said socket cavity;

said socket portion having resilient lip means extending completely around the periphery of the aperture for reducing the size thereof so that it is smaller than the axial cross-section of said cylindrical head portion, whereby said resilient lip means resiliently retains said head portion within said socket cavity, said resilient lip means including a first pair of resilient lips extending along the opposite side edges of said aperture with the transverse spacing between the lips of said first pair being slightly less than the diameter of said cylindrical head portion, said lip means also including a second pair of resilient lips extending along the opposite end edges of said aperture for reducing the length of the aperture so that it is slightly less than the axial length of the cylindrical head portion, the lips of said second pair engaging the circumferentially extending edges of said cylindrical head portion at the opposite axial ends thereof, whereby said socket cavity has a depth as measured inwardly from the lips of said second pair which is substantially the same as the diameter of the cylindrical head portion so that the cylindrical head portion when removably retained within the socket cavity does not protrude radially outwardly beyond said lip means;

whereby the relationship of said cylindrical head portion with said socket portion permits relative pivotal movement between said headed and socketed members only within a single plane so that said endoprosthesis approximates the motion of a natural ginglymus joint.

2. An endoprosthesis of claim 1, wherein the resilient lips which extend along the side and end edges of the aperture are joined together at the corners by rounded lips so that the aperture formed by said resilient lip means is of a substantially rectangular configuration but has rounded corners.

3. An endoprosthesis according to claim 1, wherein the cylindrical head portion has rounded edges defining the respective axial ends thereof, and wherein said resilient lip means includes corner lips which are formed as enlarged webs for extending between and joining the adjacent lips which extend along the side and end edges of the aperture, said corner lips creating enlarged areas of resilient engagement between said resilient lip means and said cylindrical head portion for snugly retaining same within said socket cavity.

4. An endoprosthesis according to claim 1, wherein said resilient lip means includes several enlarged resilient lip portions which are spaced around the periphery of said aperture for creating enlarged areas of resilient engagement between said lip means and said cylindrical head portion for facilitating the entry of said head portion into said socket cavity while snugly retaining said cylindrical head portion within said socket cavity.

5. An endoprosthesis according to claim 1, wherein said neck portion of said headed member is elongated in a direction parallel to the axis of said cylindrical head portion and has a length as measured in this elongated direction which is substantially equal to the axial length of said head portion less only a small distance on each end of said head portion to enable the resilient lips which extend along the end edges of said aperture to be positioned closely adjacent the edges of the neck portion.

6. An endoprosthesis according to claim 1, wherein said endoprosthesis comprises a finger joint.

7. An implantable type endoprosthesis for ginglymus joints made of materials which are substantially inert to the body, comprising:

A. a protuberant headed member comprising,
      1. a stem portion for affixing said member in bone,
      2. a neck portion on one end of said stem portion,
      3. a protuberant head portion on said neck portion, said protuberant head portion being of generally cylindrical shape and having rounded edges defining the respective ends of said head which are radiused;

B. a socketed member comprising,
1. a stem portion for affixing said member in bone,
2. a polymeric socket portion at one end of said stem portion having wall portions defining an at least partially semi-cylindrical socket cavity of radial and axial dimensions for snugly embracing said cylindrical head portion, said socket cavity being accessible through a generally rectangular aperture, said socket member having resilient lips around the entire perimeter of said aperture for reducing the size of the aperture and thereby removably retaining said cylindrical head portion within said socket cavity, and said aperture having corners which are radiused on radii larger than the radii defining the rounded edges at the ends of said head portion whereby to provide webs at said corners effective for holding the head portion in the socket cavity at the corners thereof in addition to the lips effecting such holding at the top, bottom and ends of the head portion;

C. whereby the relationship of said cylindrical head portion with said socket portion will cause pivotal motion between said members to be limited to motion in a single plane in order that said endoprosthesis will approximate the motion of a natural ginglymus joint.

* * * * *